United States Patent [19]
Arion

[11] 4,171,697
[45] Oct. 23, 1979

[54] RESPIRATOR
[76] Inventor: Henri G. Arion, 9 Bd de Stansbourg, 83100 Toulon, France
[21] Appl. No.: 841,520
[22] Filed: Oct. 12, 1977
[30] Foreign Application Priority Data
  Oct. 29, 1976 [FR] France .................. 76.33568
[51] Int. Cl.² .................................. A61M 16/00
[52] U.S. Cl. ..................................... 128/145.8
[58] Field of Search ................... 128/145.5–145.8
[56] References Cited
U.S. PATENT DOCUMENTS
| 3,507,297 | 4/1970 | Dann | 128/145.8 X |
| 3,814,093 | 6/1974 | Gregory | 128/145.8 X |

FOREIGN PATENT DOCUMENTS
| 26180 | of 1906 | United Kingdom | 128/145.8 |
| 17972 | of 1914 | United Kingdom | 128/145.8 |
| 187945 | 3/1967 | U.S.S.R. | 128/145.8 |

*Primary Examiner*—Henry J. Recla
*Attorney, Agent, or Firm*—William Anthony Drucker

[57] ABSTRACT

A portable artificial respiration device of lightweight construction for use in operations and for resuscitation. A housing includes an inlet for receiving a respirator fluid under pressure, a conduit for communicating with a patients respiratory system and an outlet for communication with the atmosphere. A rotatable distributor valve within the housing comprises a tubular member having an opening at one end which continuously communicates with the conduit. An opening in the wall of the tubular member when rotated to be adjacent the inlet provides a path for the respirator fluid to the patient for inspiration and when positioned adjacent the outlet provides an expiration path from the patient to the atmosphere. A variable speed drive under electronic speed control rotates the member to determine the inspiration and expiration rate of the patient when coupled to the device.

4 Claims, 4 Drawing Figures

RESPIRATOR

BACKGROUND TO THE INVENTION

The subject matter of the invention concerns an artificial respiration device for operations and resuscitation.

It is designed to make a light-weight, portable and independent piece of apparatus, immediately usable in all places and making it possible to provide both respiration under deep anaesthesia and resuscitation.

In devices known up to now, used not only in surgery, in operating theaters, but on all fixed or mobile equipment, the respirator apparatus had complex installations and required considerable sources of energy; the accessories required much handling before use, which necessitated the employment of specialists for adjustments and use.

The device according to the invention overcomes these drawbacks and makes it possible to make available to any practitioner or even first-aid man artificial respiration apparatus which is immediately usable to provide both respiration under deep anaesthesia and first aid.

SUMMARY OF THE INVENTION

A portable artificial respiration device of lightweight construction for use in operations and for resuscitation comprising a housing having an inlet for receiving a respirator fluid under pressure, a conduit for communication with a patients respiratory system and an outlet for communication with the atmosphere; a rotatable distributor valve located within the housing adjacent the inlet, conduit and outlet said valve comprising a cylindrical tubular member having an opening at one end continuously communicating with the conduit and including an opening within the tubular wall of said member which opening when positioned adjacent the inlet due to the rotation of said member provides a path for the respirator fluid to the patient during inspiration and when positioned adjacent the outlet provides an expiration path from the patient to the atmosphere; and variable speed drive means for rotating the valve member, said drive means including an electronic speed control, a motor receiving an output signal from said speed control and a step down gear for reducing the rotational speed of the drive from the motor, the speed control being variable to control the rotation rate of said member to select the inspiration and expiration rate of the patient when coupled to the device.

BRIEF DESCRIPTION OF THE DRAWINGS

On the attached drawings, given as a non-limiting example of one of the forms of embodiment of the subject matter of the invention.

DESCRIPTION OF PREFERRED EMBODIMENT

Figure 1:
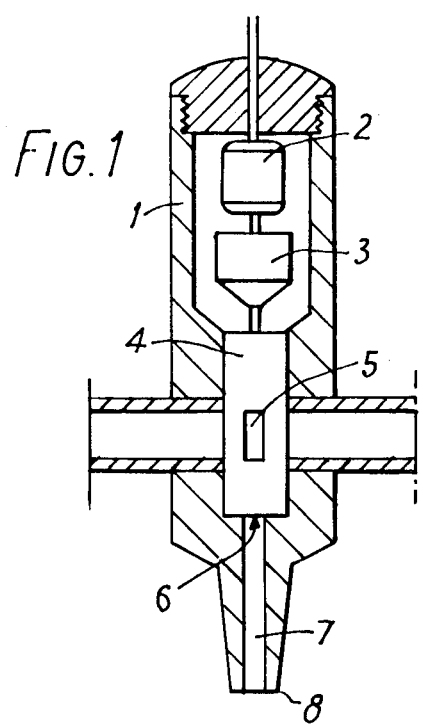
FIG. 1 shows, seen in section and in elevation, the positioning of the components.
Figure 2:
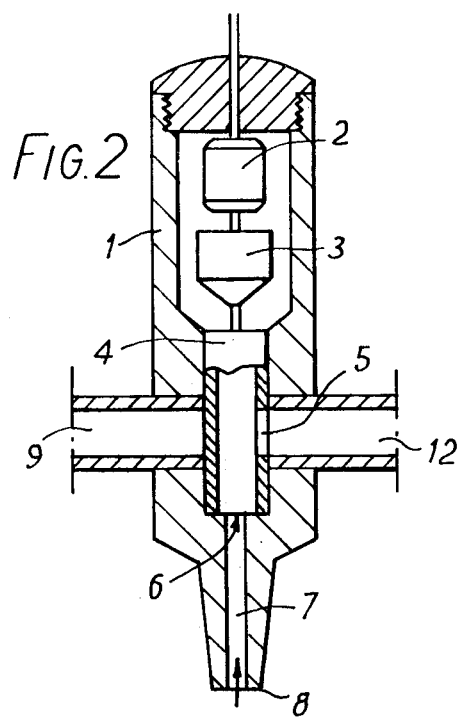
FIG. 2 is a longitudinal section of the distributor system.
Figure 3:
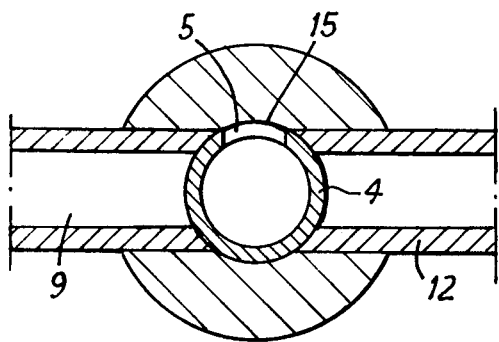
FIG. 3 shows a cross section of the distributor plug.
Figure 4:
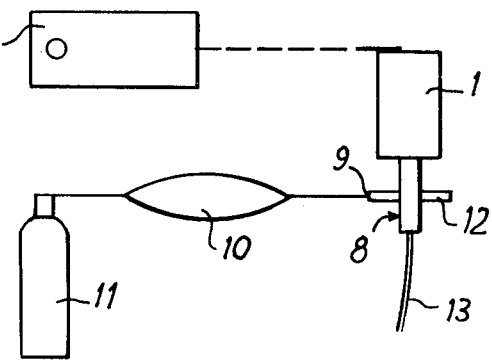
FIG. 4 is a general view of the apparatus.

The distributor, FIGS. 1, 2, 3, consists of a housing 1 containing a motor 2 with step-down gear 3. This step-down gear drives a tubular unit 4 or plug, cylindrical in section, with a shaped opening 5 and an open base 6 adjacent a conduit 7 forming an end-piece 8 on which, FIG. 4, the tracheal probe 13 or mask is connected.

Conduit 9 forms an end-piece and can be connected to a deformable respiratory pouch 10 itself taking a gas mixture such as oxygen contained under pressure with a relief valve at the output of cylinder 11 in order to have about 50 grams pressure.

This flexible pouch or bladder 10 can be inflated with air, by mouth or by any other means.

Conduit 12 is connected with the open air.

Valve 4 rotates at the speed set by the electronic control (pulse emitter) 18 and channels the current generated by a simple 1½ volt battery to the motor, which thus runs at a given speed. When the opening 5 is opposite the conduit 9 the air or gas is sent at the pre-set pressure into conduit 8 and tracheal probe 13. Mechanical intake or inspiration takes place at increasing and decreasing speed depending on the speed of rotation.

When sector 15 is passed, FIG. 3, conduit 8 communicates with the open air through conduit 12, and normal, passive and progressive expiration then occurs.

The cycle continues in perfect synchronisation, continuously and smoothly and without air shock with a succession of inspirations and expirations comparable in regularity, volume and rate with these obtained up to now with the most complex apparatus.

However the shapes, dimensions and arrangements of the different components may vary within the limit of the equivalents, as may the materials used to manufacture them, without thereby altering the general concept of the invention which has just been described.

I claim:

1. A portable artificial respiration device of lightweight construction for use in operations and for resuscitation comprising:
   (a) a housing having an inlet for receiving a respirator fluid under pressure, a conduit for communication with a patient's respiratory system and an outlet for communication with the atmosphere;
   (b) a rotatable distributor valve located within the housing adjacent the inlet, conduit and outlet said valve comprising a cylindrical tubular member having an opening at one end continuously communicating with the conduit and including an opening within the tubular wall of said member which opening when positioned adjacent the inlet due to the rotation of said member provides a path for the respirator fluid to the patient during inspiration and when positioned adjacent the outlet provides an expiration path from the patient to the atmosphere; and
   (c) variable speed drive means for rotating the valve member, said drive means including an electronic speed control, a motor receiving an output signal from said speed control and a step down gear for reducing the rotational speed of the drive from the motor, the speed control being variable to control the rotation rate of said member to select the inspiration and expiration rate of the patient when coupled to the device.

2. A device according to claim 1 wherein the inlet is connected to receive the respirator fluid from a tank under constant pressure via a deformable container.

3. A device according to claim 2 wherein the deformable container comprises a flexible pouch.

4. A device according to claim 1 wherein the conduit is connected to a tracheal probe for coupling to the patient.